(12) United States Patent
Kukawka et al.

(10) Patent No.: US 10,292,637 B2
(45) Date of Patent: May 21, 2019

(54) SYSTEM AND METHOD FOR COGNITION-DEPENDENT ACCESS CONTROL

(71) Applicant: OTORIZE. LTD, Jerusalem (IL)

(72) Inventors: Andres Kukawka, Ra'anana (IL); Isaac Samuel Hassan, Jerusalem (IL)

(73) Assignee: OTORIZE, LTD, Jerusalem (IL)

( * ) Notice: Subject to any disclaimer, the term of this patent is extended or adjusted under 35 U.S.C. 154(b) by 0 days.

(21) Appl. No.: 15/742,549

(22) PCT Filed: Jul. 14, 2016

(86) PCT No.: PCT/IL2016/050758
§ 371 (c)(1),
(2) Date: Jan. 8, 2018

(87) PCT Pub. No.: WO2017/009836
PCT Pub. Date: Jan. 19, 2017

(65) Prior Publication Data
US 2018/0199877 A1 Jul. 19, 2018

Related U.S. Application Data

(60) Provisional application No. 62/192,587, filed on Jul. 15, 2015.

(51) Int. Cl.
*A61B 5/16* (2006.01)
*A61B 5/01* (2006.01)
(Continued)

(52) U.S. Cl.
CPC ................ *A61B 5/165* (2013.01); *A61B 5/01* (2013.01); *A61B 5/02055* (2013.01);
(Continued)

(58) Field of Classification Search
CPC ......... G06F 21/31; G06F 21/316; A61B 5/16; A61B 5/161; A61B 5/162; A61B 5/163; A61B 5/165; A61B 5/167
See application file for complete search history.

(56) References Cited

U.S. PATENT DOCUMENTS 6,466,232 B1 * 10/2002 Newell .................... G06F 1/163
345/3.1
6,874,127 B2 * 3/2005 Newell .................... G06F 1/163
706/14
(Continued)

OTHER PUBLICATIONS

International Search Report of Application No. PCT/IL2016/050758 dated Nov. 7, 2016.
(Continued)

*Primary Examiner* — Van T Trieu
(74) *Attorney, Agent, or Firm* — Pearl Cohen Zedek Latzer Baratz LLP (57) ABSTRACT

A cognitive ability level identification device is disclosed. The device is configured to present cognitive test to a user and to measure the user's response to the test. When the user fails the test, the device is configured to prevent the user from operating equipment and/or take any subsequent action, activity or process or to prevent the user from entering secured locations due to poor cognitive performance. A method for evaluating the user's cognitive performance is disclosed, by presenting to the user cognitive tests and comparing the user's actual performance to pre acquired cognitive performance baseline.

15 Claims, 5 Drawing Sheets

(51) Int. Cl.
*A61B 5/0205* (2006.01)
*A61B 5/18* (2006.01)
*G16H 50/20* (2018.01)
*G16H 10/20* (2018.01)
*A61B 5/00* (2006.01)

(52) U.S. Cl.
CPC .............. *A61B 5/162* (2013.01); *A61B 5/163* (2017.08); *A61B 5/167* (2013.01); *A61B 5/18* (2013.01); *G16H 10/20* (2018.01); *G16H 50/20* (2018.01); *A61B 5/0022* (2013.01); *A61B 5/6893* (2013.01); *A61B 2560/0266* (2013.01)

(56) References Cited

U.S. PATENT DOCUMENTS

| | | | |
|---|---|---|---|
| 8,049,631 B1 | 11/2011 | Edwards | |
| 2002/0078204 A1* | 6/2002 | Newell | G06F 1/163 709/225 |
| 2005/0053904 A1 | 3/2005 | Shephard et al. | |
| 2011/0012732 A1 | 1/2011 | Farkash | |
| 2011/0212422 A1 | 9/2011 | O'Donnell et al. | |
| 2011/0304465 A1 | 12/2011 | Boult | |
| 2012/0112879 A1 | 5/2012 | Ekchian | |
| 2014/0259130 A1* | 9/2014 | Li | G06F 21/31 726/6 |

OTHER PUBLICATIONS

European Search Report of Application No. EP 16 82 3986 dated Feb. 4, 2019.

* cited by examiner

SYSTEM AND METHOD FOR COGNITION-DEPENDENT ACCESS CONTROL

CROSS-REFERENCE TO RELATED APPLICATIONS

This application is a National Phase Application of PCT International Application No. PCT/IL2016/050758, International Filing Date Jul. 14, 2016, entitled "System and Method for Cognition-Dependent Access Control", published on Jan. 19, 2017 as International Patent Publication No. WO 2017/009836, claiming the benefit of U.S. Provisional Patent Application No. 62/192,587, filed Jul. 15, 2015, all of which are hereby incorporated by reference.

BACKGROUND OF THE INVENTION

Places requiring certain level of granted authorization in order to enter them, equipment requiring certain level of skillfulness in order to operate it and operations requiring certain level of awareness in order to safely carry them out are all exposed to hazards if the cognitive ability of the authorized person is not within a specified range, or is otherwise impaired. Premises requiring access permit or equipment requiring level of skill and the like may be protected against unauthorized entrance or unauthorized operation using ID verification means as are well known in the art. Such ID verification means may be of high quality thus ensuring that a person who was not authorized in advance will be identified and further will be precluded from taking the action he/she is not authorized to do. However, such verification means verify the identity of the person but not his/her cognitive capability, for example, whether the person is cognitively impaired as a result, for example, of the consumption of alcohol or narcotics. Thus, a person who is otherwise authorized to take an action involving high level of risk or hazard and is in low level of cognitive ability—for example, who is drunk—may be allowed to take the risky operation or to enter a confined area regardless of his/her actual cognition capability.

There is a need for system and methods for detecting and analyzing on-going level of cognitive ability in order to be able to bar an authorized person with too low cognitive ability from entering controlled premises, from taking otherwise authorized actions, operate equipment, drive any type of vehicle and the like.

SUMMARY OF THE INVENTION

A cognitive level identification device for identifying cognitive capabilities of a user according to embodiments of the present invention is disclosed comprising a controller, a memory unit adapted to store controller executable code, an input device adapted to receive user inserted input data and control commands and output device (140) adapted to present a cognitive level capability test to a user and to provide an enable/disable signal to a cognitive-dependent controlled unit. The controller is configured to present to the user a cognitive capability level test by executing code stored in the memory unit, and to provide enable signal to the cognitive-dependent controlled unit when the user passes the cognitive test. The cognitive-dependent controlled unit may be a device or service that require assurance of the level of cognitive ability of the user before allowing the user to operate it, such as a car or a harmful equipment. In other cases, the cognitive-dependent controlled unit may be enable/disable unit that controls access to access-controlled premises, such as a highly classified plants.

The cognitive identification device may comprise, according to embodiments of the present invention, storage unit for storing computer executable programs and data and a sensors unit capable of sensing and providing data indicative of at least one of the following physical variables: movements of the device, location changes of the device, orientation status, and temperature whether ambient temperature, in-device temperature, temperature of the user of the device or any combination thereof.

The cognitive identification device may comprise, according to embodiments of the present invention, a communication unit adapted to provide bidirectional communication capability with the device, for transmitting and receiving data to/from at least one remote unit.

According to embodiments of the invention one of the at least one remote units is the cognitive-dependent controlled unit.

According to embodiments of the invention at least one additional unit of the at least one remote units is a central service unit configured to store, and to provide to the cognitive level identification device, at least one of: user ID parameters, user cognitive base line, user cognitive base line threshold and a list of users enrolled to use the cognitive level identification device.

A method for controlling cognitive level based permission to allow or disallow an action which leads to any device activity according to embodiments of the present invention is disclosed comprising presenting a cognitive test to a user, measuring the cognitive performance of the user in response to the presented test, comparing the cognitive performance of the user to a cognitive base line of the user, and providing enable signal when the user passes the cognitive test, which will allow operation of a device or devices and/or allow entrance to controlled premises, operation of a vehicle or similar.

According to additional embodiments of the present invention the cognitive presented to the user is one of a list comprising: presenting to the user a task in which the user is instructed to follow a line on a touch screen with his/her finger, presenting to the user a task in which the user is instructed to follow an object that is moving on a touch screen with a finger, and presenting to the user during a short pre-defined time period a graphical image, then the image is graphically blocked or covered and the user is required to respond to a YES/NO question related to graphical image, wherein the time during which the user performs the task is recorded, and wherein the cognitive level is calculated based on the task performance time.

According to further embodiments of the present invention the method comprising measuring and recording the accuracy of the user in following a line on the screen.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Figure 1:
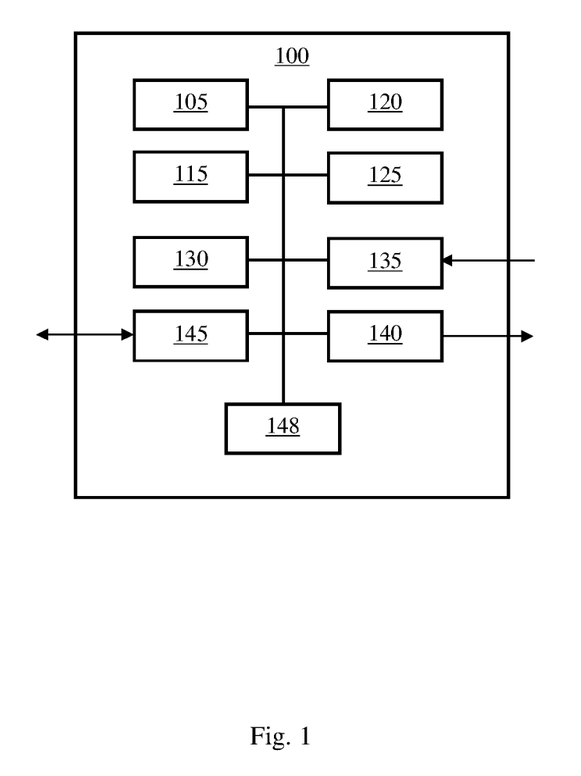
FIG. 1 is showing a high level block diagram of an exemplary computing device according to embodiments of the present invention.

Reference is made to FIG. 1, showing a high level block diagram of an exemplary computing device 100 according to embodiments of the present invention. Computing device 100 may be used to provide tools and means for identifying whether the cognitive capability of a person is above a defined level and therefore he/she may be allowed to activate (or otherwise perform an operation requiring that the person will be in a sufficient cognition capability. Computing device 100 may include a controller 105 that may be, for example, a central processing unit processor (CPU), a chip or any suitable computing or computational device, an operating system 115, a memory 120, an executable code 125, a storage 130, input devices 135, output devices 140, communication unit 145 and status sensors unit 148. Controller 105 may be configured to carry out methods described herein, and/or to execute or act as the various modules, units, etc. More than one computing device 100 may be included in a system according to embodiments of the invention, and one or more computing devices 100 may act as the various components of a system. For example, each of the portable devices described herein may be, or may include components of computing device 100. For example, by executing executable code 125 stored in memory 120, controller 105 may be configured to carry out a method of providing cognitive exam to a user.

Operating system 115 may be or may include any code segment (e.g., one similar to executable code 125 described herein) designed and/or configured to perform tasks involving coordination, scheduling, arbitration, supervising, controlling or otherwise managing operation of computing device 100, for example, scheduling execution of software programs or enabling software programs or other modules or units to communicate. Operating system 115 may be a commercial operating system.

Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 120 may be or may include a plurality of, possibly different memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be an application that manages a portable device as further described herein. Although, for the sake of clarity, a single item of executable code 125 is shown in FIG. 1, a system according to embodiments of the invention may include a plurality of executable code segments similar to executable code 125 that may be loaded into memory 120 and cause controller 105 to carry out methods described herein. For example, units or modules described herein may be, or may include, controller 105 and executable code 125.

Storage 130 may be or may include, for example, a hard disk drive, a solid state drive (SSD), solid state (SD) card, a Blu-ray disk (BD), a universal serial bus (USB) device or other suitable removable and/or fixed storage unit, adapted to store non-transient data executable by controller 105. Content may be stored in storage 130 and may be loaded from storage 130 into memory 120 where it may be processed by controller 105. In some embodiments, some of the components shown in FIG. 1 may be omitted. For example, memory 120 may be a non-volatile memory having the storage capacity of storage 130. Accordingly, although shown as a separate component, storage 130 may be embedded or included in memory 120.

Input devices 135 may be or may include data input means such as touch screen, keypad, keyboard and the like, capable of inputting data and control commands, or any suitable input device. It will be recognized that any suitable number of input devices may be operatively connected to computing device 100 as shown by block 135.

Output devices 140 may include one or more displays or monitors, speakers, vibrating means, visual, auditory and tactile means and/or any other suitable output devices. It will be recognized that any suitable number of output devices may be operatively connected to computing device 100 as shown by block 140. Any applicable input/output (I/O) devices may be connected to computing device 100 as shown by blocks 135 and 140.

Communication unit 145 may be any unit allowing bidirectional communication of device 100 with other devices, for transmitting and receiving data. Control commands and the like. The communication handled by communication unit 145 may be performed over wire system. May be wireless or may be carried over mixed communication infrastructure. Typically, the communication may be wireless, using any known means and protocols such as WiFi, Bluetooth, NFC, ZigBee, Z-WAVE, cellular communications, RFID, infrared (IR) communication and the like.

Status sensors unit 148 may comprise one or more status indicators, sensors and measurement means capable of sensing and indicating movements, location changes, orientation status, temperature (whether ambient temperature, in-device temperature, temperature of the user of device 100 or any combination thereof), images (such as a camera), heart rate, direction of look sensor such as smart glass, and the like.

Computing device 100 may be, according to embodiments of the invention, a smartphone or a wearable computing. Accordingly such embodiment of computing device 100 may be worn on the user's wrist, on the user's neck, on the user's cloth, and the like. Such embodiment of computing device 100 may be adapted to provide audible and/or visible data and instructions to the user and may further be adapted to receive response, data and any other type of input from the user. For example, computing device 100 may be worn on the user's wrist, may be adapted to present data and instructions on the device's screen and may be adapted to receive input from the user through the touch screen of device 100. According to some embodiments of the present invention device 100 may be embodied as part of a smartphone, using the smartphone's input, output and position and orientation means, it's computing and storage means and its communication means.

Computing device 100 may be in operative communication with other devices and systems for sending information, data and control commands and for receiving information, data and optionally control commands.

Computing device 100 described above may be used for presenting a cognitive test or assignment that needs to be performed by a user. The performance of the assignment (or test) by the user may be evaluated as to the time it takes the user to complete, or the accuracy of the performance (for example how accurate the user follows a curvature on a screen by his/her finger). The magnitude of success may be recorded for later use.

Figure 2:
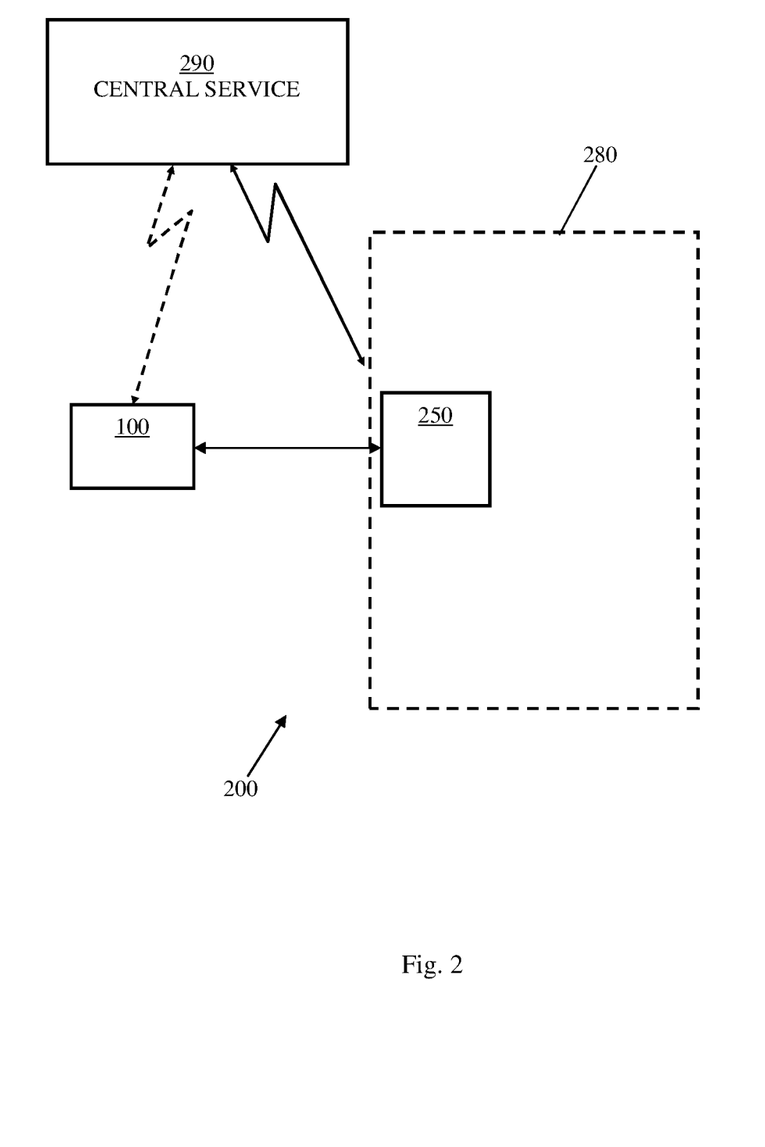
FIG. 2 schematically depicts a system for controlling cognitive-based authorization process, according to embodiments of the present invention.

Reference is made to FIG. 2, which schematically depicts system 200 for controlling cognitive-based authorization process, according to embodiments of the present invention. Cognitive-based authorization control system 200 may comprise authorization enable/disable unit 250 adapted to control the authorization requiring resources of controlled system 280. For example, controlled system 280 may be premises the entrance to which requires that the entering person will be an authorized person. According to additional embodiments of the present invention controlled system 280 may be a vehicle, a boat, a plane and the like and enable/disable unit 250 may be an immobilizer unit of the vehicle. Enable/disable unit 250 may be adapted to receive indication from computing device 100 indicative that the verified user's cognitive ability passed a pre-defined level. Upon receipt of such indication enable/disable unit 250 may further verify if the person requiring authorization is an authorized person in which case authorization signal may be issued allowing the user to perform or carry out the operation requiring authorization and/or to enter the premises requiring entrance permit. In an alternative embodiment enable/disable unit 250 may require the user to enter a unique code, such a PIN immobilizer numerical code, after the cognitive capability level was approved, in order to complete the authorization process.

Computing device 100 may have stored in storage 130 programs that when executed require a user of computing device 100 to pass cognitive exam in order to prove that the user's cognitive capability level is not below a defined threshold. Such exam may be presented to the user as a pre-condition before authorization is given.

System 200 may further comprise central service unit 290 in operational communication with controlled premises/system 280 and optionally in operational communication with computing unit 100. Central service unit 290 may be embodied as a computing unit on a remote server, comprising associated storage means (not shown), or be embodied as a cloud computing resource, or the like. Some features and roles of central service unit 290 will be described in details with regards to FIGS. 3A and 3B herein below.

Controlled access is typically based on means and methods for ensuring that the person requesting to exercise his/her permission to access secured location or to operate protected system is, indeed, and authorized person. However, there may be situations where the authorized person is not fully capable of operating the protected system, or is not fully capable of consciously exercising his/her permission. For example, the ID of a person may be approved for operating a high-risk system yet that person may be under the influence of Narcosis (regardless of substance or cognitive ability) and therefore despite being approved based on ID, may be unable to safely operate that high-risk system. In another example, a person may be authorized to enter a secured location where top secret documents are handled based on his/her ID, but that person may be in a mental status that may place the top secrets in risk despite the granted authorization. The disadvantage of ID authorization systems that are based on physical key, electronic key, password or biometric means is solved according to embodiments of the present invention by presenting a cognition level test to the person and granting full authorization only if the test is passed. It would be appreciated by those skilled in the art that the term "controlled access" as is used throughout this specification relates to any system, premises, equipment, location and the like the access to which, in the meaning of entrance, getting in, being able to open or to operate, is controlled in order to prevent unauthorized operation or entrance taken by unauthorized people or by authorized people who are not in their sufficient cognitive awareness.

Access control systems should be able to complete authorization evaluation process within a reasonably short time in order to make the system usable. Physical ID testing systems are known for long time and mostly are adapted to complete ID testing process within few seconds. The completing part of access authorization that is based on cognitive ability should also last no longer than few seconds, in order to make the authorization system usable.

According to embodiments of the present invention cognition ability testing may require performing enrollment stage after which the user requesting permission to access controlled location or system may be requested to exhibit his/her cognitive ability by passing a short cognition test. The test duration and the approval time should sum to a reasonably short time.

Figure 3A:
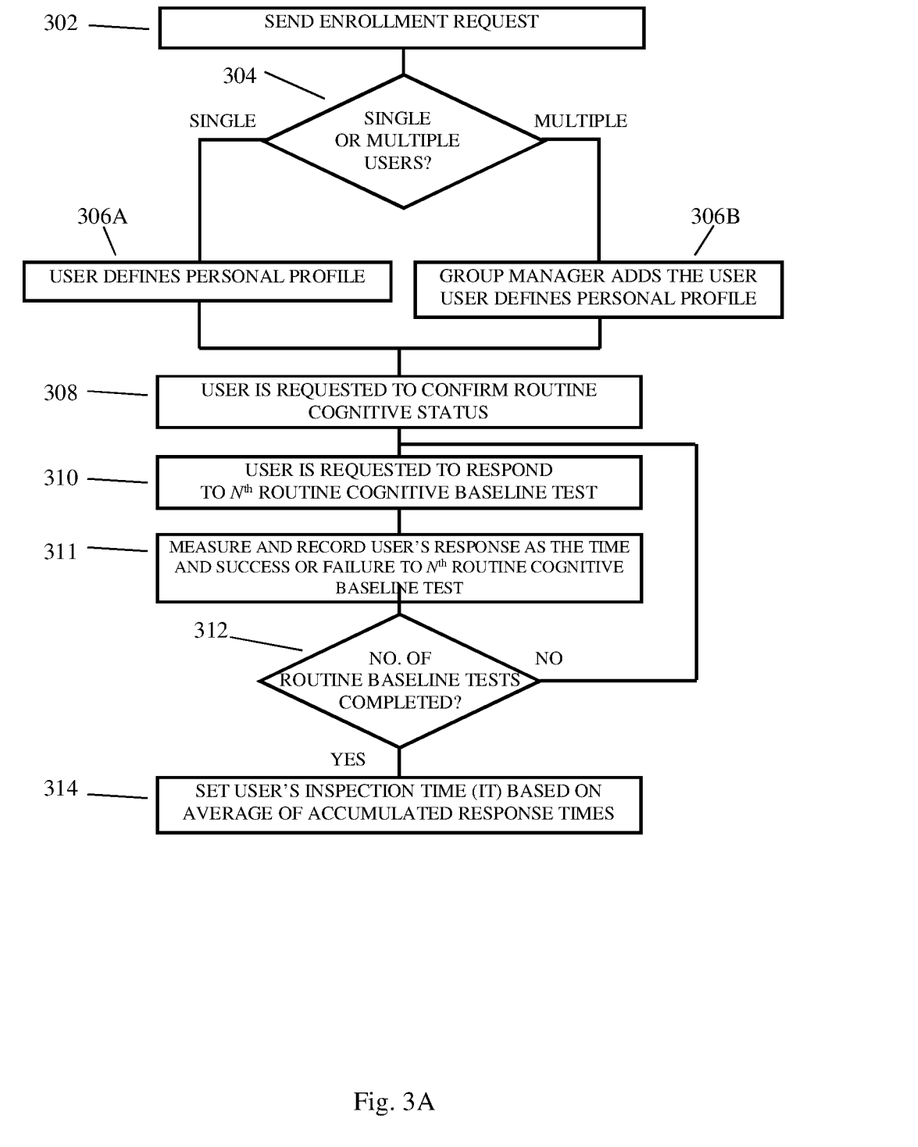
FIG. 3A is a flow diagram depicting user enrollment process, according to embodiments of the present invention.

In order to properly evaluate cognition ability of a person his/her base cognition ability should be recorded in order to draw a comparison base line. During the enrollment process the user may be requested to perform a task the time for completion if which is dependent on the level of cognition ability. After the user confirms he/she is in routine cognition status (for example—being sober), the user may be requested to perform cognition ability test, one time or more times, in order to establish personal cognition base line for the user. For example, the base line may be the average time it takes to the user to complete the task/tasks presented to him/her. Reference is made to FIG. 3A which is a flow diagram depicting user enrollment process, according to embodiments of the present invention. In order for a user to enroll for a cognition ability-based controlled access/operation the user may send a request to enroll (block 302). The enrollment process may be carried out on the user's computing device, such as the user's smartphone, in case the user is the only one requesting cognition-based controlled access/operation for a specific location or system. In case more than one user is expected to enroll to a controlled access/operation for that specific location or system, the enrollment process may be carried out on a central server or service, such as central service unit 290 in FIG. 2. In decision point 304 a single user enrolling to system 200 is requested to enter certain personal data items to define his/her personal user profile (block 306A). In such case the user's personal profile data may be saved only on the user's computing device (such as computing device 100). In case there are multiple users wishing to enroll to the cognition ability-based controlled access/operation (MULTIPLE exit at decision point 304) a group manager entity defined in the central service is requested to approve the enrollment request of the specific user and then that user is requested to enter his/her personal profile details, which are recorded with the central service, for example in the central service storage means. After personal details have been entered and recorded, the user is requested to confirm that he/she is in a routine cognition ability state (i.e.—not drunk, not too excited, or under the effects of narcosis etc.) (block 308). This stage is essential in order to define the next process as establishing a cognition reference base line. The user may now be requested to respond to a first cognition base line evaluation test (block 310). The cognition base line evaluation test may be, or may comprise presenting to the user a task in which the user is instructed to follow a line on a touch screen with his/her finger, or to follow an object that is moving on a touch screen with a finger, or the user may be asked a question regarding a graphical image presented, then the image is blocked or covered and the question is not presented anymore the user then needs to answer the question with a Yes/No, Left/Right, Up/Down, or True/False or the like. Success or failure in such test may be defined by the time it takes for the user to complete the task, by the correctness (Correct yes/no, true/false) the task was performed, by the accuracy of performance (e.g. how accurate the user follows a line on the screen or how much he deviated from that line) or by a combination thereof. The time and accuracy of the response of the user to the presented task may be measured and recorded (block 311). The user may be requested to perform more than one test. The number of performed test is checked at decision point 312. In case the required number of test was not completed ("NO") another test is carried out. In case the required number of test was carried out ("YES") the user's personal cognitive ability level is set and recorded (block 314). The level of routine cognitive ability may be calculated based on the results of multiple cognition ability tests, for example by calculation of an average score number that represents the user's routine cognitive ability and may be used as a reference base line, or by calculating the average and upper and lower limits of response time (also known as Inspection Time (IT)—the time it takes a user to process and the task, from the time it is presented till the time the user responds). The user's reference base line may be accompanied by a relative threshold that may be set respective to the base line so that when an on-line cognition ability test is done the score of the test will be compared to the threshold. The threshold may be set requiring higher score during on-line test (high demand for sobriety) or it may be set to a lower score allowing the user to demonstrate lower level of cognition ability—as the case may be. Once a routine cognition ability level was set the enrollment process may terminate.

Figure 3B:
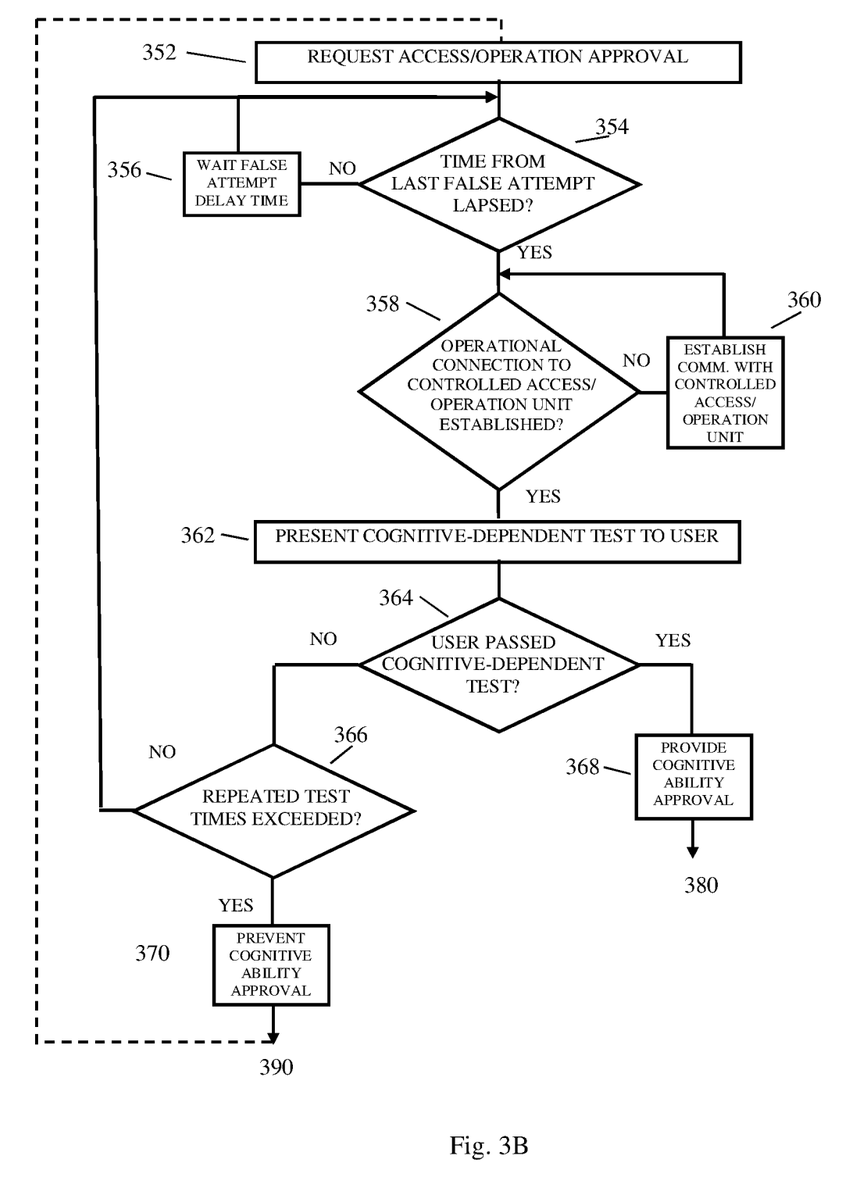
FIG. 3B is a flow diagram depicting process of requesting permission to access/operate controlled location/system, according to embodiments of the present invention.

The user's profile, as recorded during the enrollment process, may be used for setting personal IT value, for setting the time interval between repeating tests in the on-line process of FIG. 3B and the maximum number of retries for the user.

Performance of the cognitive ability test(s) may be recorded along with metadata entries, such as the location where the test was taken (for example based on GPS input, wireless network AP triangulation, etc.), time of the day/day of the week and optionally user's face picture taken during the performance of the test; manner, gait, speed, intensity of tapping/entry of PIN/answers to questions/challenges. According to some embodiments the system may track the user's successes and identify that it is taking him/her less than the previously established baseline IT. It may then be concluded that the change is due to the user became too familiar with the tests, thus the system may adjust the required IT to a lower value based on, for example, the last 10 consecutive successful tests.

A registered user of a system according to embodiments of the present invention may now exercise his/her ability to request permission to access controlled locations or premises or to operate a secured system or device or to operate a system or device safe operation of which require approved level of cognitive ability. In other embodiments the requested permission may be required in order to permit taking an action or operating a process that require approved level of cognitive ability. Reference is made now to FIG. 3B, which is a flow diagram depicting process of requesting permission to access/operate controlled location/system, according to embodiments of the present invention. The user may send a request via his/her personal computing device, such as computing device 100 of FIGS. 1 and 2 (block 352). At decision point 354 the system may check whether long enough time has lapsed since that very user last time has finally failed passing the process. In case not enough time has lapsed ("NO") the user will be instructed to wait (block 356), in order to prevent violation of the system by endless number of false trials. When long enough time has lapsed ("YES"), the system, such as system 200 of FIG. 2, will ensure operative connection between the user's computing device (such as device 100) and the controlled system/premises, such as system 280 (FIG. 2). In case the connection is not operative ("NO"), automatic or manual repeated attempts to establish the connection may be carried out (block 360), until the connection is securely established or until a timeout limit has been exceeded. When the connection between personal computing device 100 and controlled system 280 is established ("YES") the user may be presented with a cognitive ability test, as explained above (block 362). The user may respond to the test task(s) and his/her performance in responding to the presented task may be recorded and evaluated versus the routine performance of that user, considering also a potential threshold (decision point 364). In case the user passes the cognition ability test ("YES") the system may grant cognitive ability (block 368) and issue a cognitive ability signal 380. In case the user fails the test ("NO") he/she may be offered additional chances to be tested provided that the repeated number of tests in decision point 366 has not been exceeded ("NO"). In case that number of repeated test has been exceeded ("YES") a FAIL signal 390 may be issued. At this stage the user may optionally decide to repeat his/her trials to grant approval of his/her cognitive ability and return to block 352.

During each of the stages depicted in FIG. 3B or at the end of which, data representing the performance of the user during the exercising of the cognitive ability test, may be measured, collected and recorded, for later use. For example, the number of failures in performing the test, the time it took the user to run each test, the accuracy exercised during the test, etc. According to some embodiments such accumulated data may be used in order to update the user's reference base line.

In case the tested user is a person under the responsibility of another person, for example a fresh and young driver under the responsibility of an adult in a family, or a driver of a corporate fleet, failure of the tested user may be reported to the responsible managing user for further actions that may be taken by the responsible person.

Figure 4:
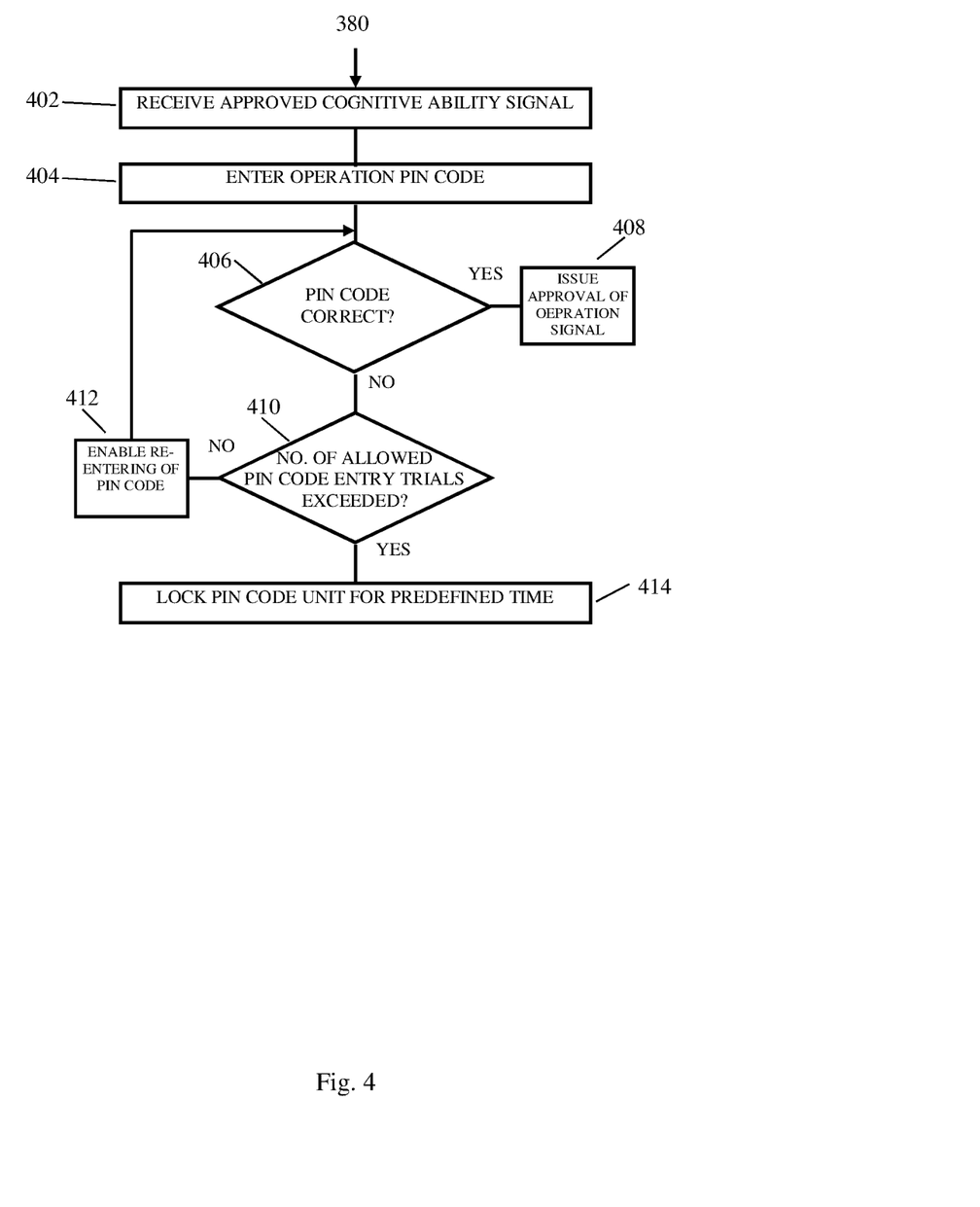
FIG. 4 is a schematic block diagram depicting process of operating a controlled system requiring both cognitive ability approval and PIN code entering stage, according to embodiments of the present invention.

Success in passing the cognitive ability test may now enable the user to proceed towards operation of the operation controlled system or to access the access controlled premises. In case the operation controlled system may further require entering PIN code in order to disable a vehicle's immobilizer unit, or identify the user for entry/pass through a door/gate or access to a device or other activity and such. Reference is made now to FIG. 4, which is a schematic block diagram depicting process of operating a controlled system requiring both cognitive ability approval and PIN code entering stage, according to embodiments of the present invention. Cognitive ability approval may be issued as explained with respect to FIG. 3B above and issuance of signal 380 may represent such approval. Once signal 380 is received (block 402) the user may enter the relevant PIN code, for example in unit 250 of FIG. 2 (block 404). The PIN code is examined (decision point 406) and in case the PIN code is correct ("YES") a signal approving operating the system, for example—igniting the vehicle's engine, may be delivered (block 408). In case the entered PIN code is incorrect ("NO") the user may retry to enter the PIN code and the number of retries is examined in decision point 410. When the maximal number was not exceeded ("NO") the user is enabled to retry entering the code (block 412). In case the maximal number is exceeded ("YES") system 280 may be locked for example for a predefined time period (block 414) before a user may be allowed to reactivate it. As with the process of FIG. 3B, here also system 280, or system 200 may record the process of entering PIN code and may provide indications of the number of failed entered code, the time between retrials and the like, for example for updating the user's habits and updating predefined time periods, or for reporting outstanding profile of operation.

Performance of a user in a group of users, during the cognitive ability on-line test and/or during the PIN code entering process may be reported to the group manager According to embodiments of the present invention the controlled access or controlled operation may be used for enabling unlock of padlocks, for opening safes, for controlling use of guns, for controlling access to secured facilities or plants or buildings, for controlling operation of equipment requiring high level of pre-qualification, such as vehicles, heavy tractors and the like, access to hazardous stuff, and the like.

According to some embodiments of the present invention computing unit 100 may be embodied in a smartphone and communication with an access controlled system such as a vehicle may be carried out using the Bluetooth (BT) communication capability that is quite common these days both in smartphones and in vehicles. Where possible, for example based on options offered in the controlled vehicle, the stage of entering the PIN code may also be done through the computing unit 100, via the BT communication channel between computing device 100 and the controlled vehicle 250.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A cognitive level identification device (100) for identifying cognitive capabilities of a user comprising:
    a controller (105);
    a memory unit (120) adapted to store controller executable code (125);
    an input device (135) adapted to receive user inserted input data and control commands; and
    output device (140) adapted to present a cognitive level capability test to a user and to provide an enable/disable signal to a cognitive-dependent controlled unit (280),
    wherein the controller is configured to:
        present to the user the cognitive capability level test by executing code stored in the memory unit, to measure the cognitive performance of the user in response to the test, to compare the cognitive performance of the user to a cognitive base line of the user, and to provide enable signal to the cognitive-dependent controlled unit (280) when the user passes the cognitive test,
        wherein the cognitive base line of the user is established during an enrollment stage in which the user is requested to perform multiple cognition ability tests and the user's base line score is determined based on his/her inspection time.

2. The device of claim 1, further comprising:
    storage unit (130) for storing computer executable programs and data; and
    sensors unit (148) capable of sensing and providing data indicative of at least one of the following physical variables: movements of the device, location changes of the device, orientation status, and temperature whether ambient temperature, in-device temperature, temperature of the user of the device or any combination thereof.

3. The device of claim 2, further comprising:
a communication unit (145) adapted to provide bidirectional communication capability with the device, for transmitting and receiving data to/from at least one remote unit.

4. The device of claim 3, wherein one of the at least one remote unit is the cognitive-dependent controlled unit (280).

5. The device of claim 4 wherein another remote unit of the at least one remote unit is a central service unit, configured to store and provide to the cognitive level identification device (100) at least one of user ID parameters, user cognitive base line, user cognitive base line threshold and a list of users enrolled to use the cognitive level identification device (100).

6. A method for controlling approval of cognitive level based permission of a user comprising:
presenting a cognitive test to a user;
measuring the cognitive performance of the user in response to the presented test;
comparing the cognitive performance of the user to a cognitive base line of the user, wherein the cognitive base line of the user is established during an enrollment stage in which the user is requested to perform multiple cognition ability tests; and
providing enable signal when the user passes the cognitive test, to allow operation of the device or to allow entrance to the entrance controlled premises.

7. The method of claim 6, wherein the enrollment stage comprises:
receiving user specific personal profile data;
presenting to the user a task to measure the user's level of cognitive ability and recoding the user's response time and accuracy of performance;
repeating the previous step for additional predefined number of times;
calculating, based on the recorded response time and accuracy of performance of the user in the repeated tasks, user's cognitive level base line.

8. The method of claim 7 further comprising setting upper and lower thresholds for the calculated baseline.

9. The method of claim 8 further comprising:
repeating the enrollment stage for at least one more user;
recording for each user a personal cognitive performance base line and
comparing the response of the user, after failure of the test to a lower cognitive baseline threshold and signaling cognitive ability failure when the lower threshold has been achieved.

10. The method of claim 6, wherein the cognitive level based permission is to permit at least one of operating a device or a system, entering a controlled entrance to location and performing a process.

11. The method of claim 6, wherein the cognitive test presented to the user is one of a list comprising:
presenting to the user a task in which the user is instructed to follow a line on a touch screen with his/her finger,
presenting to the user a task in which the user is instructed to follow an object that is moving on a touch screen with a finger, and
presenting to the user during a short pre-defined time period a graphical image, then the image is graphically blocked or covered and the user is required to respond to a YES/NO question related to graphical image,
wherein the time during which the user performs the task is recorded, and
wherein the cognitive level is calculated based on the task performance time.

12. The method of claim 11, further comprising measuring and recording the accuracy of the user in following a line on the screen.

13. The method of claim 11, further comprising measuring and recording the accuracy of the user in following a moving object presented on the screen.

14. The method of claim 11, further comprising recording the success of the user in responding the YES/NO question.

15. The method of claim 12 further comprising repeating the test for additional predefined number of times if the user fails the test.

* * * * *